United States Patent
Wolman et al.

(10) Patent No.: US 11,446,481 B2
(45) Date of Patent: Sep. 20, 2022

(54) AXIAL PUMP PRESSURE ALGORITHM WITH FIELD ORIENTED CONTROL

(71) Applicant: HeartWare, Inc., Miami Lakes, FL (US)

(72) Inventors: Justin Wolman, Aventura, FL (US); Fernando Casas, Miami Lakes, FL (US); Carlos Reyes, Davie, FL (US); Thomas R. Johnson, Franklin, MA (US)

(73) Assignee: HEARTWARE, INC., Miami Lakes, FL (US)

( * ) Notice: Subject to any disclaimer, the term of this patent is extended or adjusted under 35 U.S.C. 154(b) by 102 days.

(21) Appl. No.: 16/405,483

(22) Filed: May 7, 2019

(65) Prior Publication Data

US 2019/0343999 A1 Nov. 14, 2019

Related U.S. Application Data

(60) Provisional application No. 62/669,525, filed on May 10, 2018.

(51) Int. Cl.
*A61M 60/857* (2021.01)
*A61M 60/50* (2021.01)
(Continued)

(52) U.S. Cl.
CPC .......... *A61M 60/50* (2021.01); *A61M 60/419* (2021.01); *A61M 60/82* (2021.01); *A61M 60/857* (2021.01); *A61M 2205/3331* (2013.01)

(58) Field of Classification Search
CPC .............. A61M 1/1086; A61M 1/1008; A61M 1/1015; A61M 1/1036; A61M 2205/3331;
(Continued)

(56) References Cited

U.S. PATENT DOCUMENTS

| 5,385,581 | A | | 1/1995 | Bramm et al. |
| 5,928,131 | A | * | 7/1999 | Prem .................. F04D 13/0646 |
| | | | | 310/90.5 |

(Continued)

FOREIGN PATENT DOCUMENTS

| EP | 1481699 A1 * | 12/2004 | .......... A61M 1/1015 |
| EP | 1481699 A1 | 12/2004 | |

(Continued)

OTHER PUBLICATIONS

International Search Report and Written Opinion dated Aug. 6, 2019, for corresponding International Application No. PCT/US2019/031123; International Filing Date: May 7, 2019 consisting of 13-pages.

(Continued)

*Primary Examiner* — Joseph M Dietrich
*Assistant Examiner* — Michael T. Holtzclaw
(74) *Attorney, Agent, or Firm* — Shumaker & Sieffert, P.A.

(57) ABSTRACT

A method of controlling an implantable blood pump including a housing having a proximal portion including an inlet, a distal portion including an outlet, and an impeller therein, the method including detecting when a pressure in the housing exceeds a pressure threshold and executing a first vector control command to displace the impeller axially in a distal direction from a primary position to a secondary position different than the primary position in response to the pressure exceeding the pressure threshold.

21 Claims, 8 Drawing Sheets

(51) Int. Cl.
*A61M 60/82* (2021.01)
*A61M 60/419* (2021.01)

(58) Field of Classification Search
CPC ...... A61M 1/122; A61M 1/12; A61M 1/1001;
A61M 1/1025; A61M 1/1031; A61M
2205/3334; A61M 2205/3341; A61M
1/101; A61M 5/14236
See application file for complete search history.

(56) References Cited

U.S. PATENT DOCUMENTS

| | | | |
|---|---|---|---|
| 6,302,661 | B1 | 10/2001 | Khanwilkar et al. |
| 6,595,762 | B2 | 7/2003 | Khanwilkar et al. |
| 3,007,254 | A1 | 8/2011 | LaRose et al. |
| 8,636,638 | B2 | 1/2014 | Timms |
| 9,427,508 | B2 | 8/2016 | Reyes et al. |
| 9,492,601 | B2 | 11/2016 | Casas et al. |
| 9,511,179 | B2 | 12/2016 | Casas et al. |
| 9,561,313 | B2 | 2/2017 | Taskin |
| 10,426,879 | B2 | 10/2019 | Farnan |
| 10,660,998 | B2 * | 5/2020 | Hodges ............... A61M 1/086 |
| 10,732,583 | B2 | 8/2020 | Rudser |
| 11,131,968 | B2 | 9/2021 | Rudser |
| 11,185,682 | B2 | 11/2021 | Farnan |
| 2002/0094281 | A1 | 7/2002 | Khanwilkar et al. |
| 2003/0163019 | A1* | 8/2003 | Goldowsky ......... A61M 1/1015 600/16 |
| 2005/0025630 | A1* | 2/2005 | Ayre ..................... A61M 1/101 417/53 |
| 2007/0253842 | A1* | 11/2007 | Horvath ................ F04D 13/064 417/350 |
| 2009/0067989 | A1 | 3/2009 | Estes |
| 2012/0245680 | A1 | 9/2012 | Masuzawa et al. |
| 2012/0245681 | A1 | 9/2012 | Casas et al. |
| 2014/0066691 | A1* | 3/2014 | Siebenhaar ............. A61M 1/12 600/16 |
| 2014/0100413 | A1 | 4/2014 | Casas et al. |
| 2014/0288352 | A1* | 9/2014 | Yanai ................... A61M 1/122 600/16 |
| 2014/0357937 | A1 | 12/2014 | Reyes et al. |
| 2016/0166211 | A1 | 6/2016 | Brown et al. |
| 2016/0235898 | A1 | 8/2016 | Kanai et al. |
| 2017/0165407 | A1 | 6/2017 | Farnan |
| 2017/0185054 | A1 | 6/2017 | Rudser |
| 2017/0340788 | A1 | 11/2017 | Korakianitis et al. |
| 2018/0085507 | A1* | 3/2018 | Casas .................. A61M 1/1036 |
| 2019/0231952 | A1* | 8/2019 | Casas .................. A61M 1/1012 |

FOREIGN PATENT DOCUMENTS

| | | | | |
|---|---|---|---|---|
| WO | WO-2008106103 A2 * | 9/2008 | ............ | A61M 1/101 |
| WO | 2010118476 A1 | 10/2010 | | |
| WO | WO-2010118476 A1 * | 10/2010 | ........... | F04D 29/042 |
| WO | 2016130944 A1 | 8/2016 | | |
| WO | WO-2016187057 A1 * | 11/2016 | .......... | A61M 1/1013 |
| WO | WO-2017032751 A * | 3/2017 | .......... | A61M 1/1086 |
| WO | WO-2017120453 A1 * | 7/2017 | .......... | A61M 1/1036 |

OTHER PUBLICATIONS

International Preliminary Report on Patentability from International Application No. PCT/US2019/031123, dated Nov. 10, 2020, 7 pp.
Response to Communication Pursuant to Rules 161(1) and 162 EPC dated Dec. 17, 2020, from counterpart European Application No. 19725522.7, filed May 31, 2021, 16 pp.

* cited by examiner

AXIAL PUMP PRESSURE ALGORITHM WITH FIELD ORIENTED CONTROL

CROSS-REFERENCE TO RELATED APPLICATION

This application claims the benefit of U.S. Application Serial No. 62/669525, filed May 10, 2018.

FIELD

The present technology is generally related to blood pumps, and more particularly, to a method of controlling an impeller within a blood pump.

BACKGROUND

Mechanical Circulatory Support Devices ("MCSDs"), such as ventricular assist devices, are commonly used to assist the pumping action of a failing heart. Typically, an MCSD includes an implantable blood pump that is surgically implanted in a patient's body, the blood pump having a housing with an inlet, an outlet, and a rotor mounted therein. The inlet is connected to a chamber of the patient's heart, typically the left ventricle, whereas the outlet is connected to an artery, such as the aorta. Rotation of the rotor drives blood from the inlet towards the outlet and thus assists blood flow from the chamber of the heart into the artery. One exemplary blood pump is the MVAD® pump.

As blood flows through the blood pump, a differential pressure is created across the pump which is subject to increasing relative to a normal pressure, such as upon the existence of a suction condition or occlusion within the pump. At least one known method of controlling a rotor or impeller in response to a pump's flow rate change is provided in commonly owned U.S. Pat. No. 9,511,179B2, the disclosure of which is hereby incorporated in its entirety. For example, such disclosure describes a method of operating a blood pump using a control circuit that detects a low flow condition, characterized by a low flow rate, and commands a drive circuit of the pump to cause a momentary reduction in the pump speed in order to cure the low flow condition. In some circumstances, however, it may be harmful to wait until the low flow condition is detected before implementing corrective measures.

SUMMARY

The present invention provides a blood pump system including an implantable blood pump having a housing including an inlet and an outlet opposite the inlet, the housing defining a housing axis extending from the inlet to the outlet, an impeller suspended within the housing and being rotational around the housing axis, and a motor for rotating the impeller. In addition, the blood pump system may include a controller including a control circuit, the control circuit being in communication with the blood pump and being configured to detect a pressure across the pump when the pressure crosses a pressure threshold, and, in response to the pressure crossing the pressure threshold, the controller being configured to displace the impeller from a first position to a second position different than the first position using a vector control method.

In another embodiment, the present invention provides a method of controlling an implantable blood pump including a housing having a proximal portion including an inlet cannula, a distal portion including an outlet, and an impeller therein, the method including detecting when a pressure in the housing exceeds a pressure threshold and executing a first vector control command to displace the impeller axially in a distal direction from a primary position to a secondary position different than the primary position in response to the pressure exceeding the pressure threshold.

In another embodiment, the present invention provides a method of controlling an implantable blood pump including a housing having a proximate portion including a mechanical stop, a distal portion opposite the proximate portion, and an impeller therein, the method including detecting when the impeller is within a hazardous distance from the mechanical stop and executing a vector control command to displace the impeller axially in a distal direction from a hazardous position to a safe position away from the mechanical stop.

The techniques of this disclosure generally relate to blood pumps, and more particularly, to a method of controlling an impeller within a blood pump.

In one aspect, the present disclosure provides a blood pump system comprising an implantable blood pump. The implantable blood pump includes a housing having an inlet and an outlet opposite the inlet. The housing is defined by a housing axis extending from the inlet to the outlet. An impeller is suspended within the housing and is rotational around the housing axis. A motor for rotating the impeller is provided. A controller including a control circuit is provided.

The control circuit being is in communication with the blood pump and is configured to detect a pressure across the pump when the pressure crosses a pressure threshold. In response to the pressure crossing the pressure threshold, the controller is configured to displace the impeller from a first position to a second position different than the first position using a vector control method.

In another aspect, the disclosure provides housing that includes an inlet cannula. The inlet cannula is defined by the inlet and an inner tube surrounded by the inlet cannula. The inner tube is defined by a mechanical stop therein, and the second position is a distance away from the mechanical stop in a direction toward the outlet.

In another aspect, the disclosure provides that the distance is between 0.1 and 1.5 mm away from the mechanical stop.

In another aspect, the disclosure provides that the vector control method is a three-phase sensorless field-oriented control method including a plurality of stator windings and a plurality of alternating currents.

In another aspect, the disclosure provides that the control circuit is configured to maintain the blood pump in the second position for a time period when the pressure crosses the pressure threshold.

In another aspect, the disclosure provides that the controller is configured to displace the impeller from the second position to the first position when the pressure crosses the pressure threshold.

In one aspect, a method of controlling an implantable blood pump includes a housing having a proximal portion including an inlet cannula, a distal portion including an outlet, and an impeller. The method further includes detecting when a pressure in the housing exceeds a pressure threshold and executing a first vector control command to displace the impeller axially in a distal direction from a primary position to a secondary position different than the primary position in response to the pressure exceeding the pressure threshold.

In another aspect, the method further includes executing a maintenance control command to maintain the impeller in the secondary position for a time period, detecting a normal pressure condition of the blood pump, and executing a second vector control command to displace the impeller axially in a proximal direction from the secondary position to the primary position when the normal pressure condition is detected.

In another aspect, the method further includes moving the impeller axially in the distal direction away from a mechanical stop defined by an inner tube. The inner tube is surrounded by the inlet cannula.

In another aspect, the method further includes moving the impeller between 0.1 and 1.5 mm away from the mechanical stop.

In another aspect, the method further includes having the first vector control command be a three-phase sensorless field-oriented control method.

In another aspect, the method further includes reducing a speed of the impeller relative to an initial speed.

In another aspect, the method further includes maintaining the blood pump in the secondary position for a time period.

In another aspect, the method further includes determining whether a plurality of pump parameters are within a normal operating range.

In another aspect, the method further includes having the pump parameters include a flow and speed of the blood pump.

In one aspect, a method of controlling an implantable blood pump includes a housing having a proximate portion including a mechanical stop, a distal portion opposite the proximate portion, and an impeller. The method further includes detecting when the impeller is within a hazardous distance from the mechanical stop and executing a vector control command to displace the impeller axially in a distal direction from a hazardous position to a safe position away from the mechanical stop.

In another aspect, the method further includes detecting an adverse condition within the blood pump and detecting when the impeller is within the hazardous distance from the mechanical stop in response to the adverse condition.

In another aspect, the method further includes executing a maintenance control command to maintain the impeller within the safe position for a time period, detecting a clearance of the adverse condition of the blood pump, and executing a second vector control command to displace the impeller axially in a proximal direction from the safe position to a normal operating position.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Before describing in detail exemplary embodiments, it is noted that the claims reside primarily in combinations of system components and processing steps related to a method of controlling a blood pump. Accordingly, the system and method components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

As used herein, relational terms, such as "first" and "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

Figure 1:
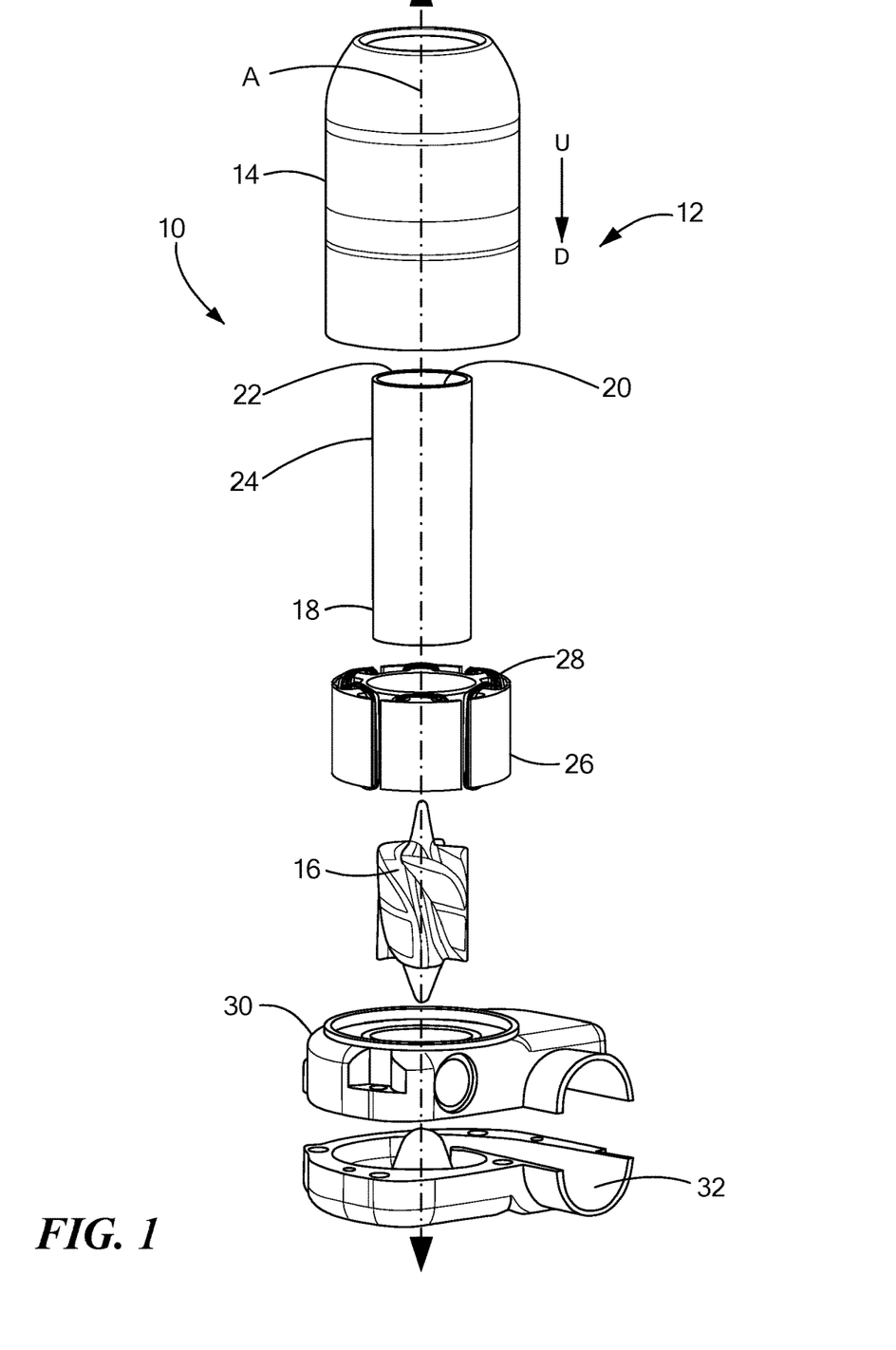
FIG. 1 is an exploded view of a blood pump including a pump housing having an impeller therein.

Referring now to the drawings in which like reference designators refer to like elements there is shown in FIG. 1 an exemplary implantable blood pump constructed in accordance with the principles of the present application and designated generally "10." The blood pump 10 may be an axial flow blood pump such as, without limitation, the MVAD® pump. Further details associated with rotary blood pumps are discussed in U.S. Pat. Nos. 8,007,254 and 9,561,313, the disclosures of which are hereby incorporated in the entirety.

In one configuration, the blood pump 10 includes a pump housing 12 having an inlet cannula 14 and an impeller 16 within the housing 12 to impel the blood. The inlet cannula 14 may include an inner tube 18 formed from a non-magnetic material, such as a ceramic. The inner tube 18 includes an interior surface 20 defining a cylindrical bore 22 for receiving the impeller 16 therein. The inner tube 18 may also include a cylindrical outer surface 24 configured to be surrounded by a stator 26 having one or more coils 28. A voltage may be applied to the coils 28 to produce an electromagnetic force to rotate the impeller 16, thus impelling the blood along a flow path from an upstream direction U to a downstream direction D.

The impeller 16 is configured to move in an axial direction relative to the housing 12 along a housing axis "A" that extends from the inlet cannula 14 through a lower housing portion 30 having an outlet 32 which may be proximate a volute. As discussed in further detail below, the method provided herein includes controlling the axial direction or position of the impeller 16 so as to move the impeller axially away from a mechanical stop located within the inner tube 18 during an adverse incident, such as suction or occlusion. Suction is an intermittent decrease in flow through the blood pump 10, whereas occlusion is a sustained decrease in flow through the blood pump 10.

The impeller 16 may be configured so that during rotation, the impeller 16 is levitated within the housing 12 by contactless bearings, such as magnetic bearings, hydrodynamic bearings or a combination of the two which produce a hydraulic and magnetic suspension system. For example, with reference to FIGS. 1 and 2, in one configuration, the pump may include a sensorless three-phase brushless direct-current (BLDC) motor 34 with the stator 26 having three windings controlled by a different respective phase U, V, W, of a power input for three-phase motor control. The BLDC motor includes an inverter circuit to convert a DC input to the three-phase output. Alternatively, the blood pump 10 may receive an alternating current (AC) three-phase input.

Figure 2:
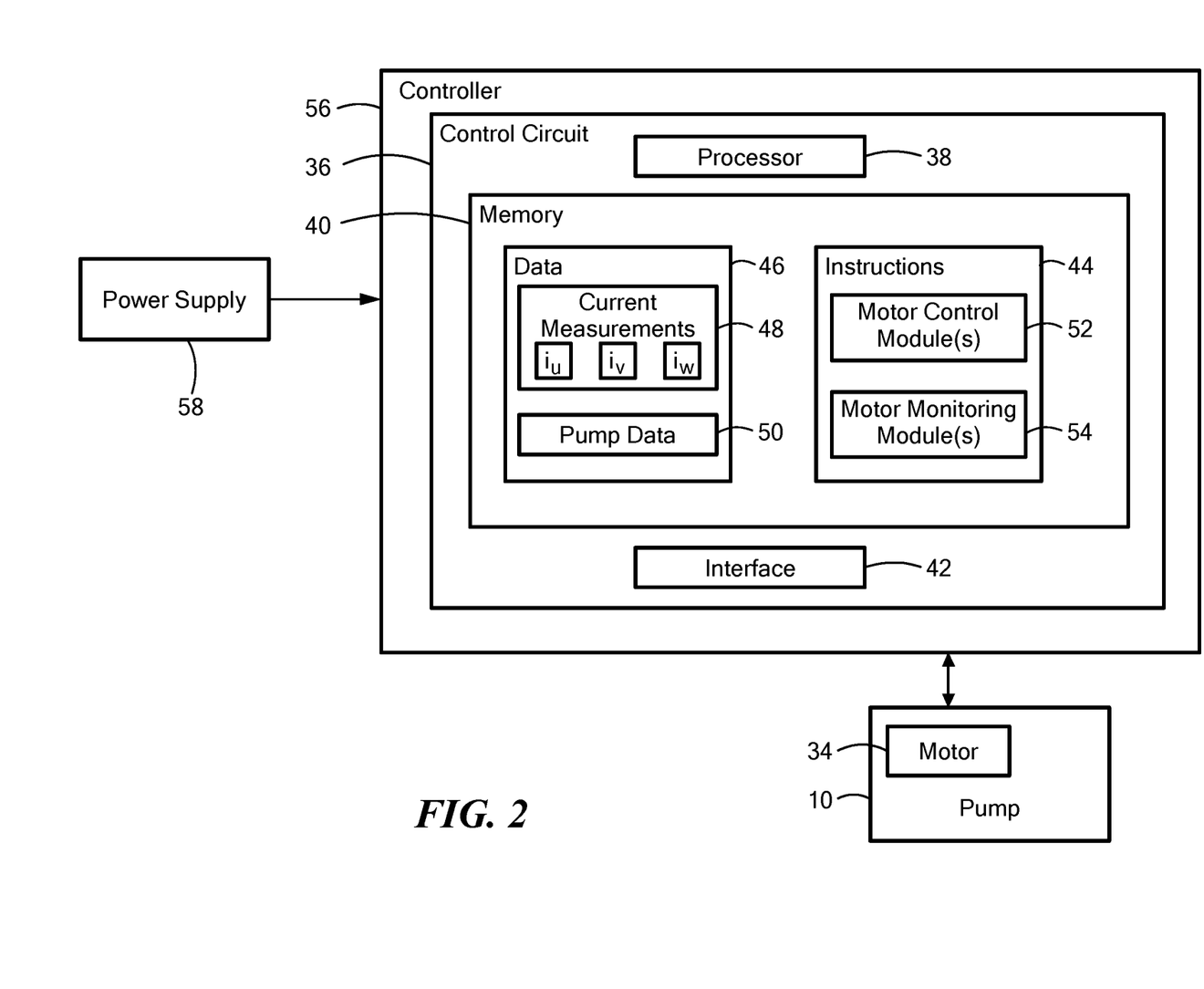
FIG. 2 is block diagram of an exemplary pump system including the blood pump of FIG. 1 and a control circuit.

With reference to FIG. 2, an example blood pump system is depicted including a control circuit 36 in communication with the blood pump 10. The control circuit 36 is configured to execute one or more of the methods steps herein and monitor and control startup and subsequent operation of the motor 34, including executing a three-phase sensorless field-oriented control (FOC) method. Exemplary FOC methods are disclosed in commonly owned and co-pending U.S. patent application Ser. No. 15/710,323, which is incorporated herein in the entirety.

In one configuration, the control circuit 36 is coupled to the motor 34 to control operation of the motor 34, such as through one or more implanted cables. The control circuit 36 includes a processor 38, a memory 40, and an interface 42 for interfacing with the motor 34. The memory 40 stores information accessible by the processor 38, including instructions 44 that may be executed by the processor 38. The memory 40 also includes data 46 that may be retrieved, manipulated or stored by the processor 38. The memory 40 may be of any type capable of storing information accessible by the processor 38, such as a hard-drive, memory card, ROM, RAM, DVD, CD-ROM, write-capable, and read only memories. The processor 38 may be any well-known processor, such as commercially available processors. Alternatively, the processor 38 may be a dedicated controller such as an ASIC.

The data 46 may be retrieved, stored or modified by the processor 38 in accordance with the instructions 44. The data may also be formatted in any computer-readable format such as, but not limited to, binary values, ASCII or Unicode. Moreover, the data 46 may comprise any information sufficient to identify the relevant information, such as numbers, descriptive text, proprietary codes, pointers, references to data stored in other memories (including other network locations) or information that is used by a function to calculate the relevant data.

The control circuit 36 includes hardware and software for controlling the various aspects of the operation of the motor 34. The control circuit 36 may be coupled to the motor 34 through the interface 42 to collect at least some of data 46 from the motor 34. For example, the data 46 may include one or more electrical current measurements 48 of the motor windings of the stator 26 (FIG. 1). The current measurements may be provided from current sensors, such as first, second and third shunts $R_1$, $R_2$, $R_3$ for measuring the respective currents $i_u$, $i_v$, $i_w$ of the motor windings. In one example, each of the shunts may be connected to a respective amplifier or programmable gain amplifier (PGA), to amplify the measured voltage across the shunt. Given the known resistance of each shunt, the amplified voltages may be converted back into current measurements. An analog to digital (A/D) converter may also be included for receiving the amplified voltages and converting them into corresponding digital signals to be received by the control circuit 36. The data 46 may include pump data 50, such as flow rate of blood exiting the pump, flow pulsatility, differential pressure across the pump, motor speed, current supplied to the motor, and the like.

The instructions 44 stored in the memory 40 may include one or more instruction sets or modules, for performing certain operations in accordance with the present disclosure. One such module may be a motor control module 52 for controlling operation of the motor 34 (e.g., increasing or decreasing current supplied to the motor), such as in accordance with the FOC routines described herein. The instructions may also include one or more motor monitor modules 54 for monitoring operation of the motor 34. Examples of motor control and monitoring modules may be found in the commonly owned and copending U.S. patent application Ser. Nos. 13/355,297, 13/951,302, 14/294,448, 14/950,467, 62/266,871 and 62/271,618, the disclosures of which are incorporated herein by reference in their entireties. The control circuit 36 may be disposed within a controller 56 which is connected to a power supply 58.

Figure 3:
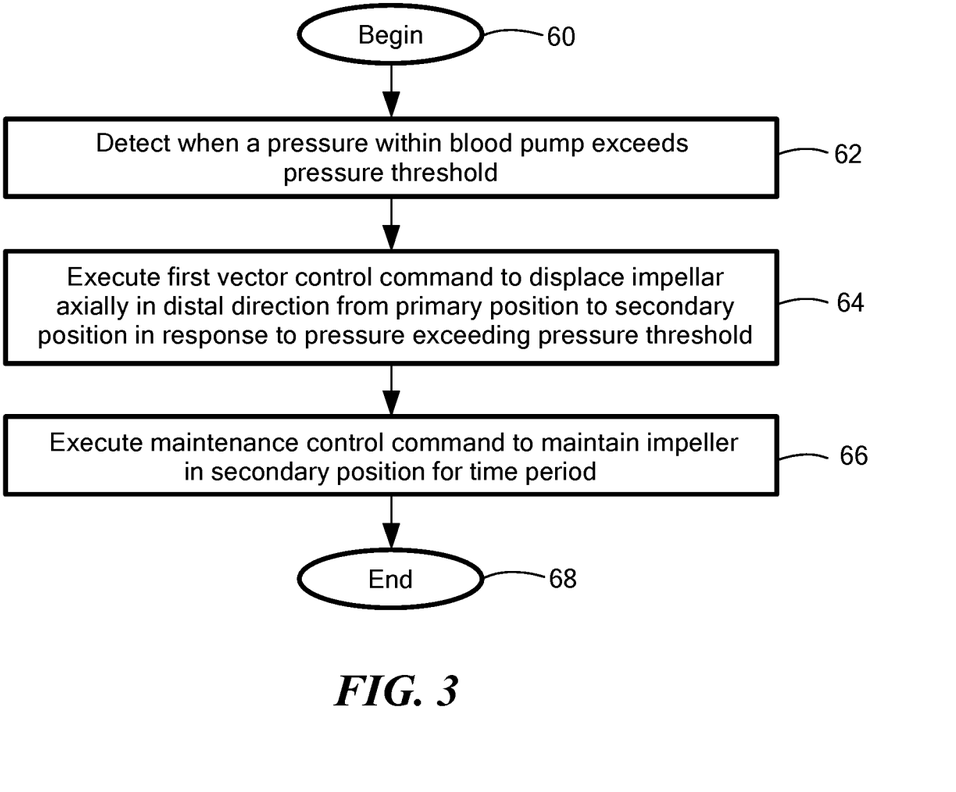
FIG. 3 is a flow chart depicting a method of controlling the blood pump of FIG. 1.

Referring now to FIG. 3, a flow chart is depicted including exemplary process steps for implementing a method of controlling the axial position of the impeller 16. The order of the process steps may vary and one or more process steps may be added and/or omitted. FIG. 3 may be viewed in conjunction with FIG. 4 depicting a perspective view of the blood pump 10 in an assembled configuration and FIG. 5 depicting a cross-sectional perspective view of the blood pump 10 taken along section A-A of FIG. 4.

In one configuration, the method begins with step 60 and proceeds directly to step 62 of detecting when a pressure in the housing 12 across the blood pump 10 exceeds a pressure threshold. The pressure threshold may be predetermined using blood pump parameters, such as speed and flow, and is indicative of a high-pressure or adverse condition, such as suction or occlusion. The pressure detection may be determined using the controller 56, the control circuit 36, and one or more modules within the control circuit 36. For example, a method of operating a blood pump using a control circuit that detects a low flow condition is described in commonly owned U.S. Patent Pub. No. 2012/0245681, the disclosure of which is hereby incorporated in the entirety. In addition, commonly owned U.S. Pat. No. 9,427,508, the disclosure of which is hereby incorporated in the entirety, discloses a method of determining whether a high-pressure condition is present in the blood pump based on determined flow rate. For example, a differential pressure value greater than a predetermined threshold pressure value may be indicative of a high-pressure condition across the pump. In lieu of or in addition to detecting the pressure threshold, step 62 may include detecting when the pump flow is outside of a designated range and/or the use of one or more sensors to measure and obtain information associated with the blood pump parameters.

Figure 4:
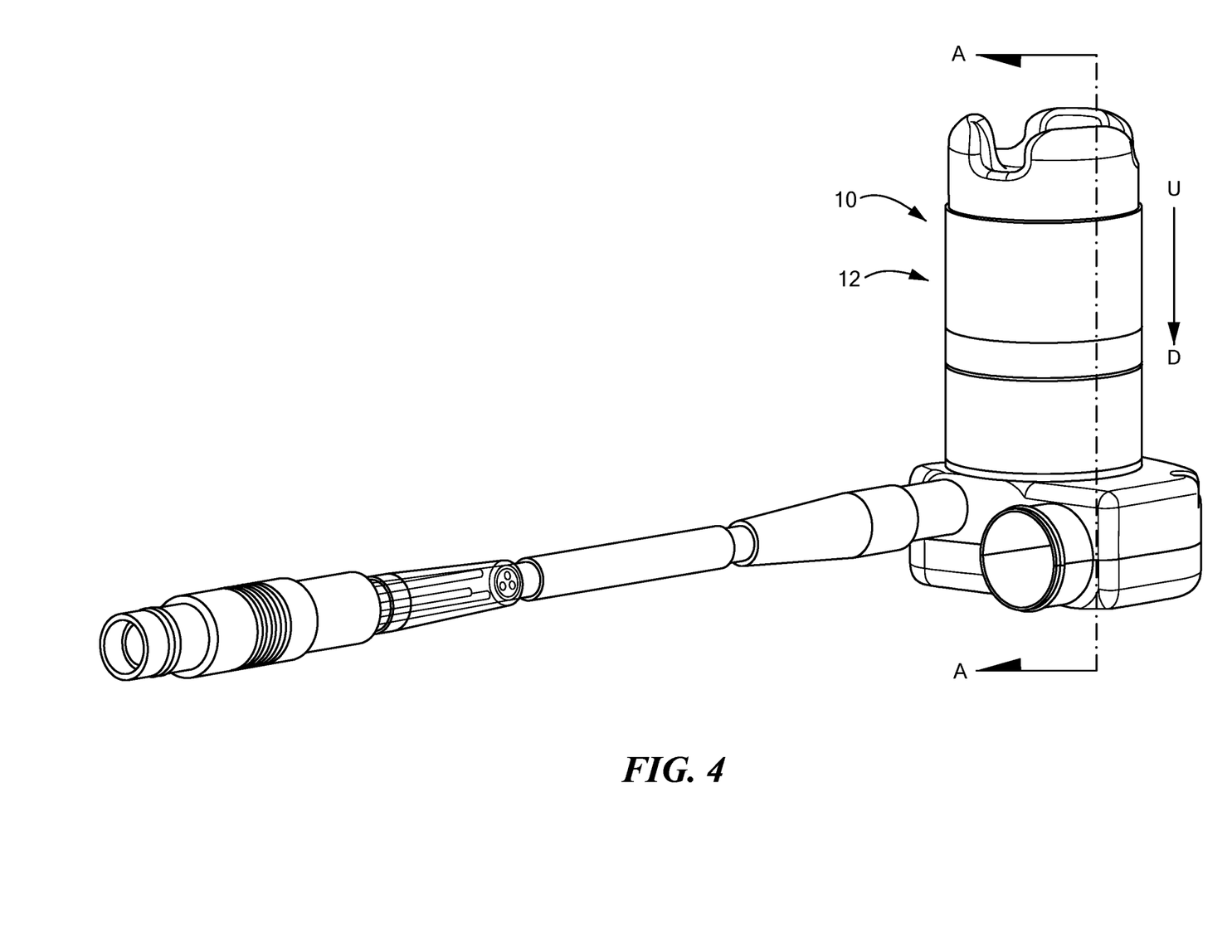
FIG. 4 is a perspective view of the blood pump of FIG. 1 in an assembled configuration.
Figure 5:
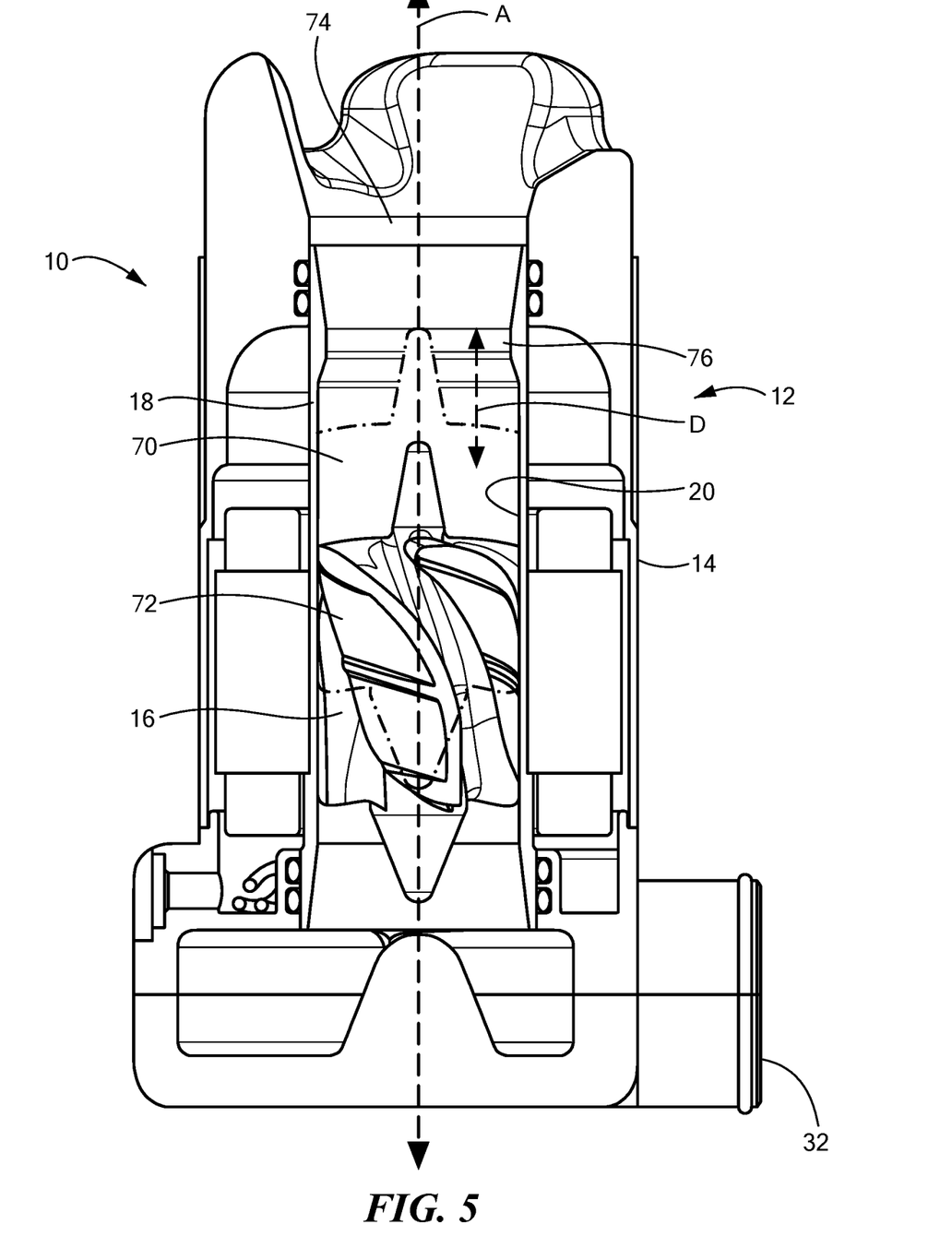
FIG. 5 is a front cross-sectional view of the blood pump of FIG. 1 taken along section A-A of FIG. 4 depicting a position of the impeller.

With reference to FIGS. 3 through 5, in one configuration, in response to the pressure crossing the pressure threshold, in step 64, the controller 56 may execute a first vector control command to displace the impeller 16 in a distal direction from a first position 70, i.e., a primary position, to a second position 72, i.e., a secondary position, different than the first position 70. The distal direction is in the downstream direction along the axis "A" from an inlet 74 toward the outlet 32 opposite the inlet 74.

In one configuration, the first vector control command is executed using a vector control method, such as the three-phase sensorless field-oriented control method described above including the set of three stator windings and the set of three alternating currents. In other configurations, the vector control method may be an alternative variable-frequency drive (VFD) control method.

As shown in FIG. 5, the second position 72 includes the impeller 16 being a distance, generally designated as "D," away from the mechanical stop 76 defined by the inner tube 18. In one configuration, the distance is between 0.1 and 1.5 mm; however, in other configurations, the distance may be between 0.1 to 2.0 mm or may be outside of this range as determined, for example, using an algorithm taking into account the dimensions of the blood pump 10, a sine waveform pattern, predetermined increments, or the like.

The mechanical stop 76 is configured to limit axial displacement of the impeller 16 within the inner tube 18. In one configuration, the mechanical stop 76 may be formed as a portion of the inner tube 18, located closer to the inlet 74 than the outlet 32, having a diameter smaller than a remaining diameter of the inner tube 18. In other words, the mechanical stop 76 may be a slope, indentation, or the like, which creates a narrow portion of the inner tube 18 configured to prevent the impeller 16 from traveling beyond the mechanical stop 76 toward the inlet 74. In other configurations, the mechanical stop 76 may be a piece of material coupled to the interior surface 20 of the inner tube 18.

Moving the impeller 16 away from the mechanical stop 76 is configured to reduce the pressure in the housing 12, prevent pressure buildup, and/or prevent the impeller 16 from contacting the mechanical stop 76 during pressure build up or the high-pressure condition while maintaining hydraulic performance.

In one configuration, the controller 56 may be configured to reduce a speed of the impeller 16 relative to an initial speed, such as when the pressure crosses the pressure threshold. The relative amount of the speed reduction may be a preselected reaction speed sufficient to reduce the pressure buildup across the blood pump 10. The preselected reaction speed may be stored in the memory 40 of the controller 56.

In step 66 (FIG. 3), the controller 56 and the control circuit 36 may be configured to execute a maintenance command to maintain the impeller 16 in the second position 72 for a time period, such as until the controller 56 detects a normal pressure condition in the blood pump 10 indicating that the high-pressure condition is resolved. For example, commonly owned U.S. Pat. No. 9,427,508, referenced above and incorporated herein, describes a method of detecting whether the blood pump is operating under a predetermined pressure threshold and within normal operating conditions. In another example, the controller 56 may be configured to determine whether one or more pump parameters, such as the flow and the speed of the blood pump 10, are within a normal operating range.

Figure 6:
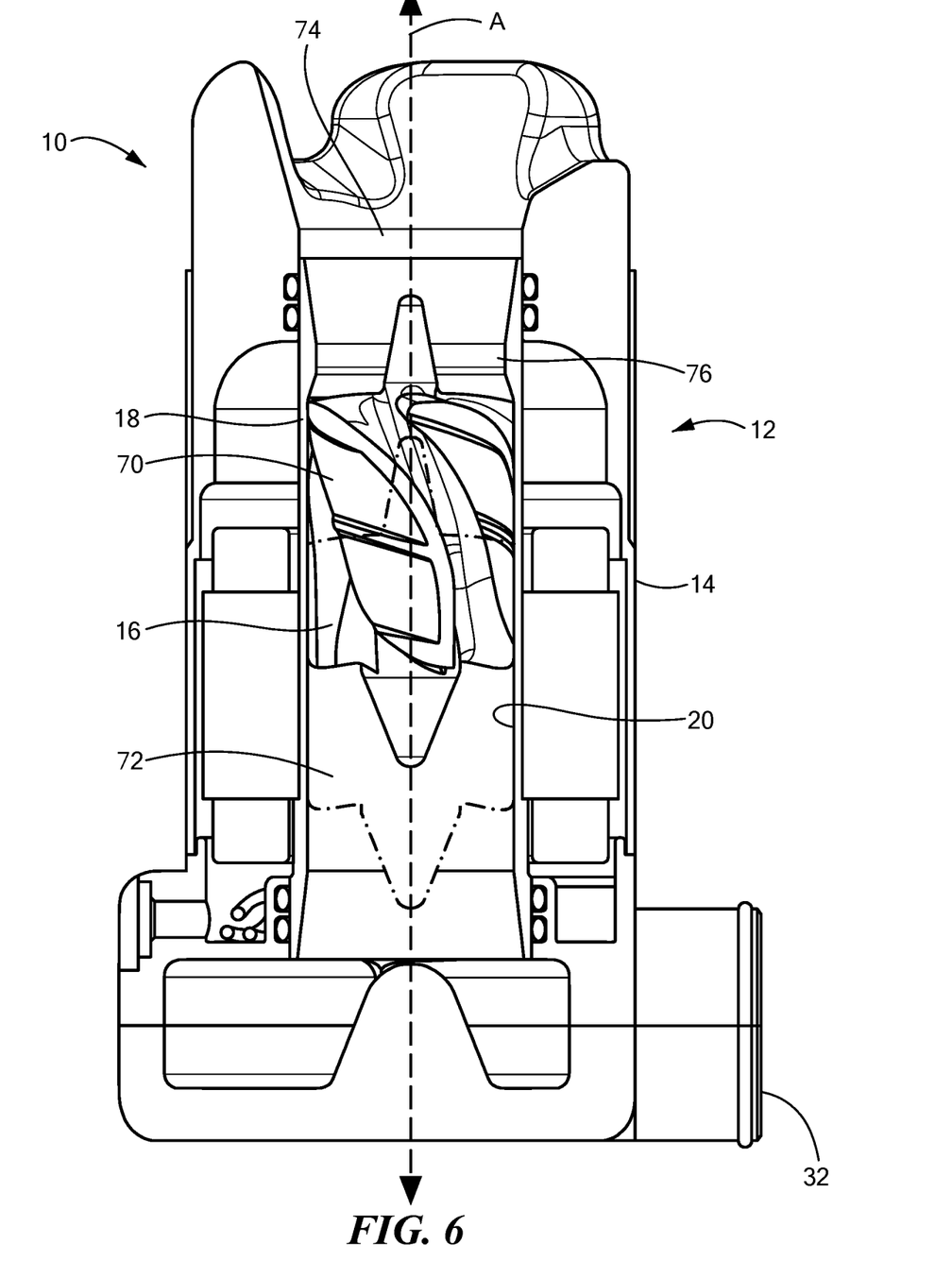
FIG. 6 is a front cross-sectional view of the blood pump of FIG. 1 taken along section A-A of FIG. 4 depicting an alternative position of the impeller.

Referring to FIG. 6, when the normal pressure across the blood pump 10 is detected, the method described herein includes the controller 56 being configured to execute a second vector control command using the control methods described above. The second vector control command is configured to displace the impeller 16 axially in a proximal direction from the second position 72 to the first position 70 wherein the blood pump 10 may resume operating under normal conditions. The method ends at step 68.

Figure 7:
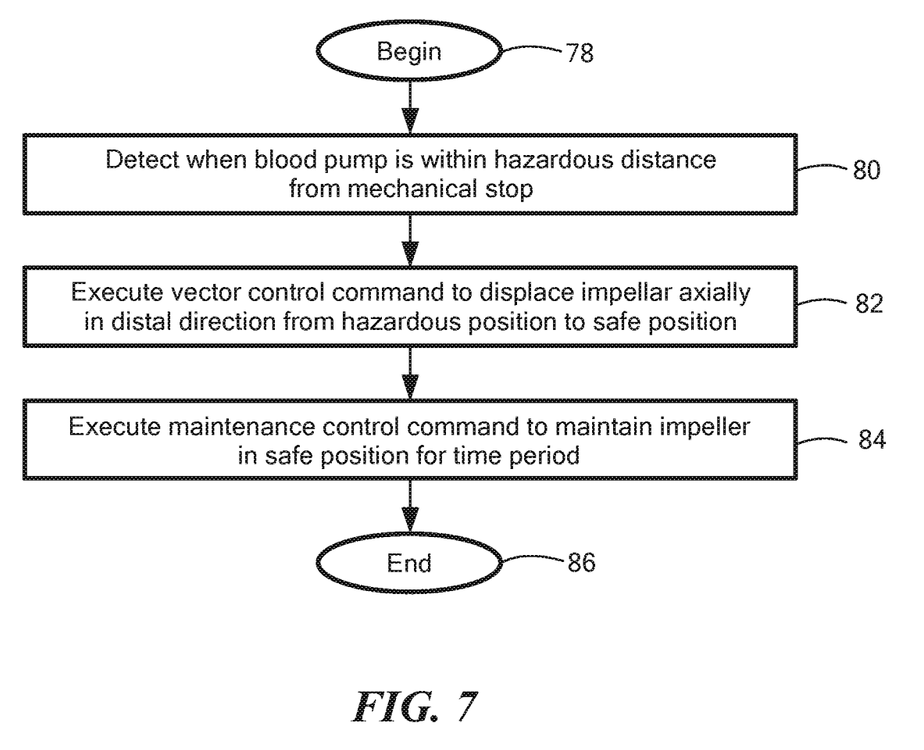
FIG. 7 is a flow chart depicting another method of controlling the impeller of the blood pump of FIG. 1.
Figure 8:
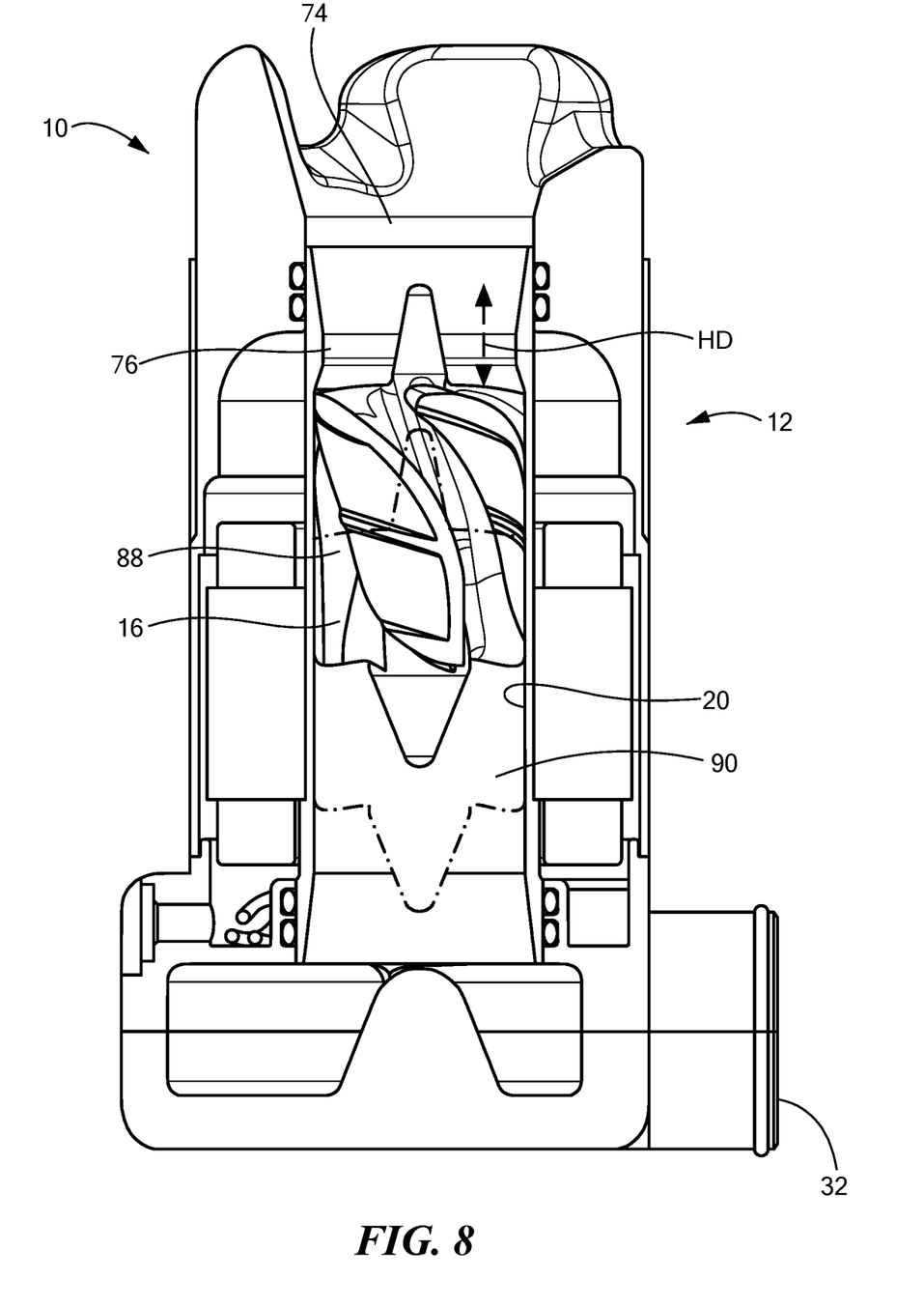
FIG. 8 is a front cross-sectional view of the blood pump of FIG. 1 taken along section A-A of FIG. 4.

With reference to FIGS. 7 and 8, in another configuration, in lieu of or in addition to the controller 56 being configured to detect when the pressure exceeds the pressure threshold, the method may begin with step 78 and proceed to step 80 of detecting when the impeller 16 is within a hazardous position 88 that is within a hazardous distance, generally designated as "HD," (FIG. 8) from the mechanical stop 76. For example, as shown in FIG. 8, the impeller 16 may be forced in a direction toward the mechanical stop 76 under an adverse or high-pressure condition. The hazardous distance may be, for example, within 0.05 to 1.5 mm of the mechanical stop 76 or when the impeller 16 contacts the mechanical stop 76.

The method of detecting the hazardous distance may be executed using the methods and components described above with respect to the pressure detection. For example, the controller 56 may be configured to detect that the impeller 16 is within the hazardous distance using the control circuit 36 and one or more modules and/or sensors. An alarm may be triggered in response to the controller 56 detecting that the pressure has exceeded the pressure threshold and/or upon detecting that the impeller 16 is located at the hazardous position 88.

In step 82, the method may include executing a vector control command, such as the first vector control command described above, to displace the impeller 17 axially in the distal direction from the hazardous position 88 to a safe position 90 away from the mechanical stop 76. The safe position 90 may be a same or similar position as the second position 72 (FIGS. 5 and 6).

In one configuration, in step 84, the method may include executing the maintenance control command to maintain the impeller 16 in the safe position for a time period, such as until the controller 56 detects that the adverse or high-pressure condition has cleared. In the safe position, the speed of the impeller 16 may also be reduced. Once the controller 56 detects a clearance of the adverse condition, the controller 56 may be configured to execute a second vector control command, such as that described above, to displace the impeller 16 axially in the proximal direction from the safe position 90 to a normal operating position which may be the first position 70 (FIG. 5). The method ends at step 86.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A blood pump system comprising:
an implantable blood pump including:
a housing having an inlet and an outlet, the housing defining a housing axis extending from the inlet to the outlet and including a mechanical stop co-axial with the housing axis;
an impeller suspended a distance away from the mechanical stop within the housing, the impeller being configured to rotate around the housing axis; and
a motor configured to cause the impeller to rotate; and
a controller including a control circuit, the control circuit being in communication with the blood pump and being configured to:
determine that a pressure across the pump crosses a pressure threshold indicative of suction, and, in response to the pressure crossing the pressure threshold indicative of suction, displace the impeller from a first position to a second position different than the first position and reduce a speed of the impeller;
maintain the impeller in the second position when the pressure crosses the pressure threshold indicative of suction; and
displace the impeller from the second position to the first position when the pressure crosses the pressure threshold indicative of a lack of suction.

2. The blood pump system of claim 1, wherein the second position is a distance away from the mechanical stop in a direction toward the outlet, the distance away being between 0.1 and 1.5 mm from the mechanical stop.

3. The blood pump system of claim 1, wherein the housing defines a downstream direction from the inlet towards the outlet, and wherein the second position is downstream of the first position.

4. The blood pump system of claim 1, wherein the first position is closer to the mechanical stop than the second position.

5. The blood pump system of claim 1, wherein the housing includes an inlet cannula defining the inlet and an inner tube surrounded by the inlet cannula, the inner tube defining the mechanical stop.

6. The blood pump system of claim 5, wherein the inner tube defines a slope or an indentation that defines the mechanical stop, or comprises an attachment that defines the mechanical stop.

7. The blood pump system of claim 5, wherein the inner tube is configured to prevent the impeller from traveling beyond the mechanical stop toward the inlet.

8. The blood pump system of claim 1, further comprising a memory storing a predetermined speed, wherein the control circuit is configured to reduce the speed of the impeller to the predetermined speed.

9. The blood pump system of claim 1, wherein the control circuit is configured to reduce the speed of the impeller to reduce the pressure in the housing.

10. The blood pump system of claim 1, wherein to displace the impeller from the primary position to the secondary position, the control circuit is configured to move the impeller 0.1 millimeters (mm) to 2 mm away from the mechanical stop.

11. A method comprising:
detecting that a pressure in a housing of a blood pump exceeds a pressure threshold indicative of suction, wherein the blood pump comprises:
the housing having an inlet and an outlet, the housing defining a housing axis extending from the inlet to the outlet and including a mechanical stop co-axial with the housing axis;
an impeller suspended a distance away from the mechanical stop within the housing, the impeller being configured to rotate around the housing axis; and
a motor configured to cause the impeller to rotate;
in response to the pressure exceeding the pressure threshold, displacing the impeller from a primary position to a secondary position different than the primary position and reducing a speed of the impeller, wherein displacing the impeller includes moving the impeller away from the mechanical stop;
maintaining the impeller in the secondary position;
detecting a non-suction pressure condition of the blood pump; and
displacing the impeller from the secondary position to the primary position when the non-suction pressure condition is detected.

12. The method of claim 11, wherein the mechanical stop is defined by an inner tube, the inner tube being surrounded by the inlet cannula.

13. The method of claim 12, wherein displacing the impeller from the primary position to the secondary position comprises moving the impeller 0.1 millimeters (mm) to 1.5 mm away from the mechanical stop.

14. The method of claim 11, wherein reducing the speed of the impeller reduces the pressure in the housing.

15. A blood pump system comprising:
an implantable blood pump including:
a housing having an inlet and an outlet, the housing defining a housing axis extending from the inlet to the outlet and including a mechanical stop;

an impeller suspended a distance away from the mechanical stop within the housing, the impeller being configured to rotate around the housing axis; and a motor configured to cause the impeller to rotate; and a controller including a control circuit configured to:

detect a suction condition of the blood pump by at least determining the impeller is at a first position within a first predetermined distance from the mechanical stop; and     in response to determining the impeller is in the first predetermined position, control the motor to reduce a speed of the impeller and displace the impeller in a distal direction from the first predetermined position to a second position further away from the mechanical stop than the first predetermined position along the housing axis.

16. The blood pump system of claim 15, wherein the control circuit is configured to:

determine a clearance of the suction condition of the blood pump; and     in response to determining the clearance of the suction condition, displace the impeller in a proximal direction relative to the second position.

17. The blood pump system of claim 16, wherein the control circuit is configured to displace the impeller in the proximal direction relative to the second position by at least displacing the impeller to a third position between the first and second positions.

18. The blood pump system of claim 15, wherein the first predetermined distance is 0.1 millimeters (mm) to 1.5 mm from the mechanical stop.

19. The blood pump system of claim 15, wherein the housing includes an inlet cannula defining the inlet and an inner tube surrounded by the inlet cannula, the inner tube defining the mechanical stop.

20. The blood pump system of claim 15, further comprising a memory storing a predetermined speed, wherein the control circuit is configured to reduce the speed of the impeller to the predetermined speed.

21. The blood pump system of claim 15, wherein the control circuit is configured to reduce the speed of the impeller to reduce the pressure across the pump.

\* \* \* \* \*